(12) United States Patent
Travis et al.

(10) Patent No.: US 8,465,464 B2
(45) Date of Patent: Jun. 18, 2013

(54) INFUSION PUMP AND SLIDE CLAMP APPARATUS AND METHOD

(75) Inventors: Lee W. Travis, Centennial, CO (US); Christina Wamsley, Denver, CO (US)

(73) Assignee: WalkMed Infusion LLC, Englewood, CO (US)

( * ) Notice: Subject to any disclaimer, the term of this patent is extended or adjusted under 35 U.S.C. 154(b) by 212 days.

(21) Appl. No.: 12/852,116

(22) Filed: Aug. 6, 2010

(65) Prior Publication Data

US 2012/0035581 A1 Feb. 9, 2012

(51) Int. Cl.
*A61M 5/00* (2006.01)

(52) U.S. Cl.
USPC .......................................................... 604/250

(58) Field of Classification Search
USPC .......................................................... 604/250
See application file for complete search history.

(56) References Cited

U.S. PATENT DOCUMENTS

| | | |
|---|---|---|
| 3,374,509 A | 3/1968 | Logan et al. |
| 4,155,362 A | 5/1979 | Jess |
| 4,460,358 A | 7/1984 | Somerville et al. |
| 4,586,691 A | 5/1986 | Kozlow |
| 4,689,043 A | 8/1987 | Bisha |
| 4,818,190 A | 4/1989 | Pelmulder et al. |
| 5,017,192 A | 5/1991 | Dodge et al. |
| 5,219,327 A | 6/1993 | Okada |
| 5,290,238 A | 3/1994 | Crass et al. |
| 5,300,044 A | 4/1994 | Classey et al. |
| 5,401,256 A | 3/1995 | Stone et al. |
| 5,437,635 A | 8/1995 | Fields et al. |
| 5,437,642 A | 8/1995 | Thill et al. |
| 5,453,098 A | 9/1995 | Botts et al. |
| 5,868,712 A | 2/1999 | Briggs et al. |
| 6,261,262 B1 | 7/2001 | Briggs et al. |
| 6,629,955 B2 | 10/2003 | Morris et al. |
| 6,840,492 B1 | 1/2005 | Boyne-Aitken |
| 2002/0165503 A1 | 11/2002 | Morris et al. |
| 2006/0129110 A1 | 6/2006 | Smith et al. |
| 2007/0270765 A1 | 11/2007 | Hasler |
| 2009/0306592 A1 * | 12/2009 | Kasai et al. ................... 604/131 |

FOREIGN PATENT DOCUMENTS

| | | |
|---|---|---|
| EP | 0718006 A1 | 6/1996 |
| JP | 2000-237308 | 9/2000 |
| WO | 2004/007015 A1 | 1/2004 |
| WO | 2006/083933 A1 | 8/2006 |
| WO | 2009/133705 | 11/2009 |

OTHER PUBLICATIONS

European Search Report for Application No. 11006387.2-2320, dated Nov. 18, 2011, 7 pages.

* cited by examiner

*Primary Examiner* — Kevin C Sirmons
*Assistant Examiner* — Bradley Osinski
(74) *Attorney, Agent, or Firm* — John R. Ley

(57) ABSTRACT

An infusion pump for metering fluid flow through an delivery tube of an infusion tubing set has an internal occlusion clamp which clamps the delivery tube to prevent the free flow of fluid through the tube when access to the delivery tube in the infusion pump is possible. To release the delivery tube from the infusion pump, a slide clamp is manually used to release the occlusion clamp to an open, non-occluding position while simultaneously occluding the delivery tube to prevent the free flow of fluid.

24 Claims, 12 Drawing Sheets

INFUSION PUMP AND SLIDE CLAMP APPARATUS AND METHOD

This invention relates to prohibiting the free flow of medicinal fluid into a patient from a delivery tube of an intravenous tubing set used with an infusion pump. More particularly, the present invention relates to a new and improved apparatus and method which uses a slide clamp to release the delivery tube from the infusion pump and simultaneously occlude the delivery tube, thereby ensuring that the delivery tube is occluded whenever the delivery tube is removed from the infusion pump.

BACKGROUND OF THE INVENTION

Intravenous tubing sets are commonly used with an infusion pump to deliver fluid medications directly into the bloodstream of a patient. Fluid, such as glucose or saline, is mixed or dissolved with a medical substance in a bag, and a delivery tube conducts the medicinal fluid from the bag into a needle or other connector which delivers the fluid into a vessel, typically a vein, of the patient. The bag is suspended above the patient so that the force of gravity acting on the fluid causes the fluid to flow through the delivery tube.

A ramp valve and a drip chamber are sometimes included in-line with the delivery tube to control the flow rate of the fluid. Although the ramp valve is useful and sufficiently accurate for some applications, it is not a fully reliable metering device. Variations in the height or head of fluid in the bag cause variations in the fluid flow rate through the delivery tube. Variations in the height of the fluid in the bag occur naturally as the fluid flows from the bag, and also occur when a pole stand which supports the bag above the patient is adjusted in height. In addition, the use of a ramp valve does not typically provide the degree of precision in fluid delivery necessary in many medical situations.

For those medical applications which require precise metering of the medicinal fluid delivered to the patient, infusion pumps are used to precisely control the amount of fluid delivered. A portion of the delivery tube is clamped or connected in the infusion pump, and the infusion pump is operated by electrical power to deliver the fluid at a precise rate. In most cases, infusion pumps are peristaltic in operation. The flexible delivery tube is compressed or pinched at two spaced-apart locations to capture a predetermined volume of fluid in the tube between the pinch points. The pinched locations are mechanically advanced at a predetermined timed rate. This wave-like movement repeats and creates a very precise flow of fluid over time.

When the infusion pump is stopped, the tube remains pinched together by the pumping mechanism to occlude the tube. No fluid can flow to the patient when the pump is stopped and the tube remains within the infusion pump. In some infusion pumps, the peristaltic pinching action occurs with respect to a door on the pump. When the door is closed, the closed door provides a working surface against which the delivery tube is pinched during the peristaltic action. When the door is opened, the delivery tube is no longer pinched because the working surface separates from the delivery tube. Opening the door under these circumstances creates the possibility of the medicinal fluid free-flowing into the patient.

To prevent the fluid from free-flowing when the door is open, infusion pumps typically include an internal occlusion clamp which pinches the delivery tube to occlude the delivery tube. Such internal occlusion clamps become effective when the door is opened. When the door is closed, the internal occlusion clamp is moved to a non-occluding position. Moving the internal occlusion clamp to the non-occluding position when the door is closed allows peristaltic movement of the fluid through the delivery tube by the peristaltic or other internal pumping mechanism.

It is necessary to remove the delivery tube from the infusion pump. Of course to do so, the door must be open to gain access to the delivery tube. Opening the door results in the internal occlusion clamp clamping the delivery tube, making it very difficult or impossible to remove the delivery tube from the infusion pump. Under these circumstances, the infusion pump must include some provision for releasing the internal occlusion clamp even though the door is open. With the delivery tube removed from the infusion pump, there is no restriction on the gravity flow of fluid from the bag through the delivery tube into the patient. Even short times of unrestricted gravity flow can introduce potentially dangerous amounts of the medicinal fluid into the bloodstream of the patient, since the flow rate through the operating infusion pump is typically much less than the gravity-induced free flow rate when the delivery tube is not restricted.

Occasionally when it is necessary to remove the delivery tube from the infusion pump, the tubing set may remain connected to the patient, giving rise to the possibility that the fluid will free-flow by gravity into the patient in an uncontrollable manner. The potential for gravity-induced free flow of fluid into the patient occurs when it is necessary to exchange one infusion pump for a different infusion pump in the case of mechanical failure of an infusion pump. Another circumstance which may give rise to gravity-induced free flow of fluid into the patient is when two bags are connected to a single tubing set and the fluid has been delivered from one of the bags. Under such circumstances, the delivery tube from the empty bag must be removed from the infusion pump and the delivery tube from the full bag substituted within the infusion pump. Under these exemplary circumstances, the fluid may flow from the bag into the patient.

To prevent overdosing the patient when the delivery tubing is removed from the infusion pump and the delivery tubing is still connected to the patient, manual clamps are usually located on the delivery tube external to the infusion pump. Closing such an external clamp prior to removing the tubing from the infusion pump avoids the free flow of fluid into the patient. Such an external clamp may be the ramp valve or a similar roll or slide clamp. However, the success of this procedure depends on the attending medical personnel closing the external clamp. Although unusual, medical personnel may become distracted and fail to close the external clamp. Medical personnel who do not have the necessary level of experience and training may simply fail to recognize the need to close the external clamp when the delivery tube is removed from the infusion pump while the delivery tube remains connected to the patient. Executing the necessary sequence of closing the external clamp before removing the delivery tube from the infusion pump may also increase the risk that relatively inexperienced medical personnel may make a mistake in the sequence of actions required.

Because of the potential for human error when using an infusion pump, certain medical standards and accreditation organizations require that infusion pumps have built-in, automatic anti-free flow capabilities. Such anti-free flow capabilities prevent the free flow of fluid through the delivery tube when the delivery tube is removed from the infusion pump or when the door to the pump is open and the peristaltic constrictions can no longer occlude the delivery tube. Such anti-free flow capability is intended to overcome the natural possibility of inadvertent human failure to clamp the delivery tube externally whenever the tubing set is removed from the infusion pump or whenever the infusion pump is manipulated in such a way that free flow through the delivery tube becomes possible.

A number of previous automatic anti-free flow mechanisms have been employed in infusion pumps. Some of those anti-free flow mechanisms are subject to unintended manipulation in such a way that the delivery tube can be removed from the infusion pump without occluding the delivery tube, thereby defeating the anti-free flow capability. Other anti-free flow mechanisms are more reliable. Regardless of the level of success in preventing gravity flow, almost all of the previous infusion pumps which possess anti-free flow capability are of considerably increased cost and complexity. The increased complexity has also increased the risk of mechanical failure, with the attendant possibility of downtime of the equipment leading to the unavailability of the equipment. The increased complexity also creates an increased risk of successfully defeating the anti-free flow capability, out of a lack of knowledge of the proper functionality of the system or from good faith attempts to remove the delivery tube under appropriate circumstances but using inappropriate techniques.

One such popular infusion pump which incorporates anti-free flow capabilities requires a slide clamp to be inserted into the pump whenever the delivery tube is loaded into the pump. The slide clamp is captured by the internal operating mechanism of the infusion pump when the door is closed, and the slide clamp becomes part of the occlusion clamp operating mechanism. Sensors within the pump detect the presence of the slide clamp as a condition for operating the pump. A complicated arrangement of moving parts within the pump moves the slide clamp relative to the delivery tube to open the delivery tube to the flow of fluid as a part of operating the internal occlusion clamp. The delivery tube is occluded when the delivery tube is forced into a narrow portion of a V-shaped notch in the slide clamp, thereby pinching the side walls of the tube together. The delivery tube is opened to the flow of fluid when the slide clamp is moved in the opposite direction where the delivery tube extends through the wide portion of the V-shaped notch.

A variety of other types of anti-free flow mechanisms are also used in infusion pumps, but these other types of anti-free flow mechanisms do not employ slide clamps. These other types of pumps and anti-free flow mechanisms have had varying degrees of success in preventing inadvertent and intentional human action from overriding the intended anti-free flow capability.

SUMMARY OF THE INVENTION

The present invention uses a slide clamp as an external manual activator for releasing or opening an internal occlusion clamp within the infusion pump to an open position, to permit removing the delivery tube from the infusion pump. Manually manipulating the slide clamp to release the internal occlusion clamp simultaneously moves the delivery tube into the narrow end of a slot in the slide clamp, thereby preventing the free flow of fluid through the delivery tube whenever the internal occlusion clamp is opened. Thus, the simple expedient of manually manipulating the slide clamp to release the internal occlusion clamp to the open position has the effect of simultaneously occluding the delivery tube and thereby achieving anti-free flow functionality. The slide clamp does not become part of the internal operating mechanism of the infusion pump. When the door of the infusion pump is closed, the door interacts with a peristaltic pump to occlude the tubing, so closing the door also releases the internal occlusion clamp without requiring the presence of the external slide clamp within the infusion pump. Medical personnel must manually move the external slide clamp relative to the delivery tube to deliver fluid to the patient, even after the internal occlusion clamp opens and the infusion pump commences operation. Requiring manual movement of the slide clamp relative to the delivery tube before the pump can operate is a further safety aspect of the invention which prevents unintended fluid delivery to the patient.

These features of the invention reduce the number of moving parts of the infusion pump, reduce the cost of the pump because of its simpler construction, make the operation of the pump simpler and safer by avoiding the necessity of performing a sequence of complicated steps to occlude and release the delivery tube, enhance safety by requiring intentional, manual action on the part of medical personnel to deliver fluid to the patient, and permit medical personnel with less training and experience to successfully operate the infusion pump in a safe and effective manner.

One aspect of the invention involves a method of preventing free flow of fluid through a delivery tube of an infusion tubing set used with an infusion pump to regulate the flow of fluid delivered to a patient. The infusion pump has an internal occlusion clamp having an occluding position for occluding the delivery tube upon gaining access to a portion of the delivery tube within the infusion pump and a non-occluding position for allowing fluid movement when the portion of the delivery tube within the infusion pump is not accessable. The method comprises locating a slide clamp on the delivery tube at a location outside of the infusion pump with the delivery tube extending initially through a non-occluding opening, and manually using the slide clamp to release the internal occlusion clamp to the non-occluding position while simultaneously moving the delivery tube from the non-occluding opening into an occluding opening in the slide clamp to occlude fluid flow through the delivery tube. Preferably, the singular manual movement of the slide clamp simultaneously releases the internal occlusion clamp and moves the delivery tube from the non-occluding opening into the occluding opening.

Other subsidiary features of the method involve moving the internal occlusion clamp to the non-occluding position by insertion movement of the slide clamp into an access opening in the infusion pump and moving the portion of the delivery tube into the occluding portion of the slide clamp by stationarily retaining a portion of the delivery tube relative to the access opening while moving the slide clamp with insertion movement; stationarily supporting a portion of the delivery tube on one side of the slide clamp while moving the slide clamp with insertion movement to move the portion of the delivery tube into the occluding opening of the slide clamp; stationarily supporting the delivery tube on at least one side of the slide clamp against a tube support to move the portion of the delivery tube into the occluding opening of the slide clamp by the insertion movement; guiding the slide clamp into the access opening by moving a projection from the slide clamp in a guide channel formed in a tube support; locking the occlusion clamp in the non-occluding position after manually moving the slide clamp to release the internal occlusion clamp; and locating the slide clamp on the delivery tube at a sufficient distance from the portion of the delivery tube contained in the infusion pump to allow manual movement of the slide clamp to the position for the insertion movement without disturbing the portion of the delivery tube contained in the infusion pump.

Another aspect of the invention pertains to an infusion pump having an internal occlusion clamp for preventing free flow of medicinal fluid through a delivery tube of an infusion tubing set used with the infusion pump to regulate the flow of fluid delivered to a patient. The infusion pump includes an internal occlusion clamp having an occluding position for occluding the delivery tube upon gaining access to a first portion of the delivery tube within the infusion pump and a non-occluding position for allowing fluid movement when the first portion of the delivery tube within the infusion pump is not accessable. The internal occlusion clamp has a movable release mechanism by which to move the internal occlusion clamp from the occluding position to the non-occluding position. The tubing set includes a slide clamp connected to a second portion of the delivery tube. The slide clamp has a non-occluding opening which does not occlude the delivery tube when located in the non-occluding opening and an occluding opening which occludes the delivery tube when located in the occluding opening. An access opening into the infusion pump allows movement of the slide clamp to release the release mechanism. At least one tube support is located adjacent to the access opening. A release tab extends from the slide clamp and is adapted to fit within the access opening by which to move the release mechanism upon insertion movement. The tube support locates the delivery tube adjacent to the slide clamp in a stationary position to move the delivery tube from the non-occluding opening into the occluding opening of the slide clamp simultaneously with insertion movement of the slide clamp sufficient to move the release mechanism of the internal occlusion clamp.

A further aspect of the invention involves a slide clamp for selectively occluding a tube. The slide clamp comprises a body having a length in a longitudinal dimension and which extends from a proximal end to a distal end, having a width less than the length in a lateral dimension perpendicular to the longitudinal dimension, and having a height less than the width in a dimension transverse to the longitudinal and lateral dimensions. The height of the body at the proximal end is greater than the height of the body at the distal end. The slide clamp includes a non-occluding opening defined in the body and an occluding opening defined in the body as an extension of the non-occluding opening. The occluding opening is positioned proximally of the non-occluding opening. The non-occluding opening has a width in the lateral dimension that is approximately equal to the diameter of the tube. The slide clamp is moveably located to selectively position the tube within either the non-occluding opening or the occluding opening. The tube is occluded when the tube is positioned within the occluding opening, and the tube is unrestricted when the tube is positioned within the non-occluding opening.

Subsidiary features of the slide clamp include a trapezoidal shaped tab located at the distal end of the body, a wedge-shaped portion formed at the proximal end of the body which extends progressively greater in height from a proximal portion of the occluding opening to the proximal end of the body, and a projection extending in the height dimension above the portion of the body in which the occluding and non-occluding openings are defined and other located distal of the non-occluding opening and proximal of the tab. A further subsidiary feature includes the combination of the slide clamp and an infusion tubing set.

A more complete appreciation of the present invention and its scope may be obtained from the accompanying drawings, which are briefly summarized below, from the following detailed description of a presently preferred embodiment of the invention, and from the appended claims.

DETAILED DESCRIPTION

Figure 1:
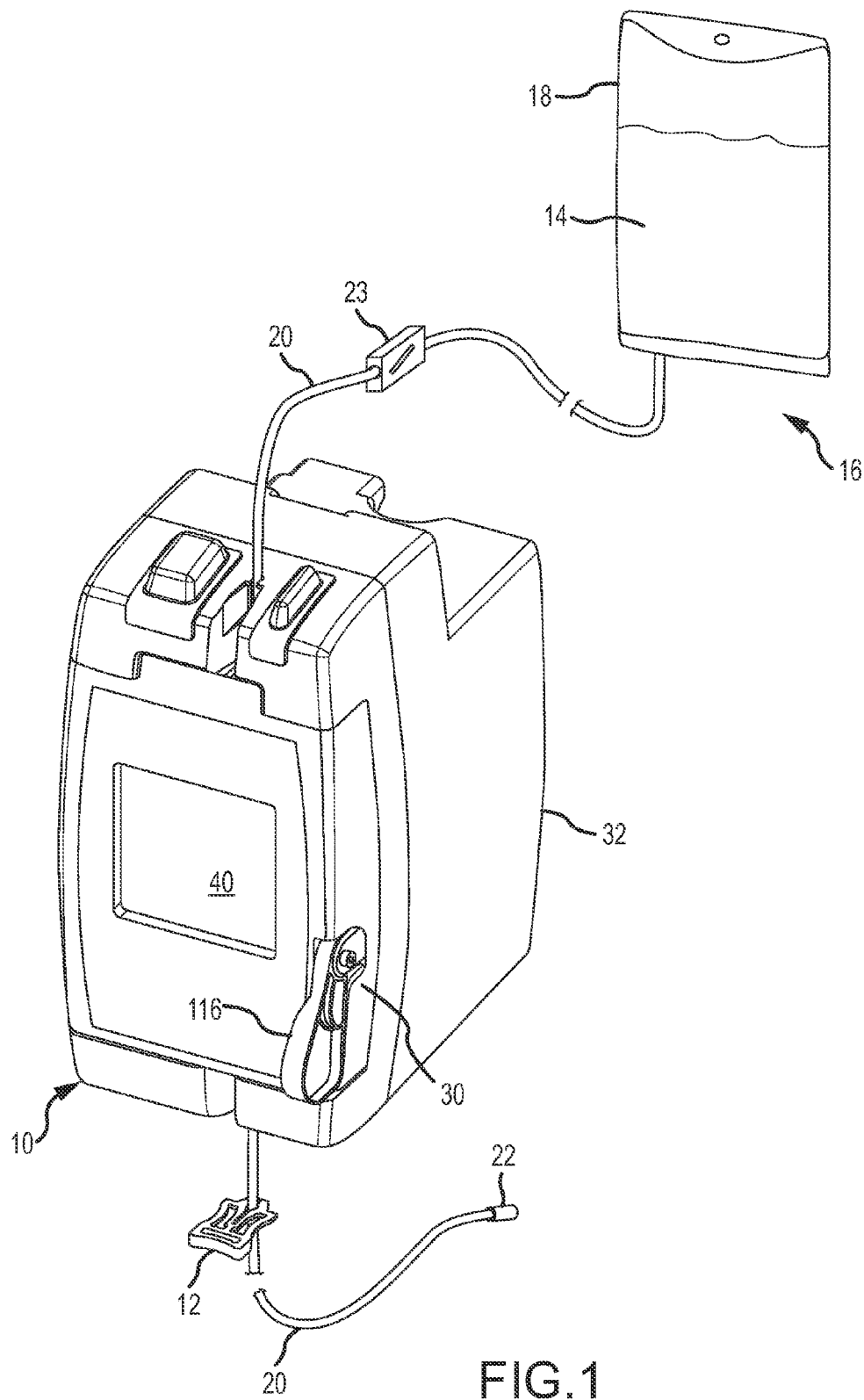
FIG. 1 is a perspective view of an infusion pump and a slide clamp which incorporate the present invention, shown with a front door of the infusion pump in a closed position and the slide clamp attached to a delivery tube of an infusion tubing set.

An infusion pump 10 and a slide clamp 12 which embody the present invention are shown in FIG. 1. The infusion pump 10 precisely meters a flow of medicinal fluid 14 through an intravenous tubing set 16 to a patient (not shown). The tubing set 16 includes a flexible and collapsible bag 18 which stores the fluid 14, and a delivery tube 20 which conducts the fluid 14 from the bag 18 to a connector 22. The connector 22 connects to a needle (not shown) inserted into a vessel, typically a vein of a patient, or to a complementary connection of a conventional vessel access device attached to the patient. A conventional ramp or roller clamp 23 is connected to the delivery tube 20 to constrict the delivery tube 20 and thereby control the cross-sectional size of an opening through the delivery tube through which the fluid 14 flows. The roller clamp 23 will typically be moved to a non-restricting position when the infusion pump 10 is in operation, because the infusion pump meters the flow of fluid 14 through the delivery tube 20.

Figure 4:
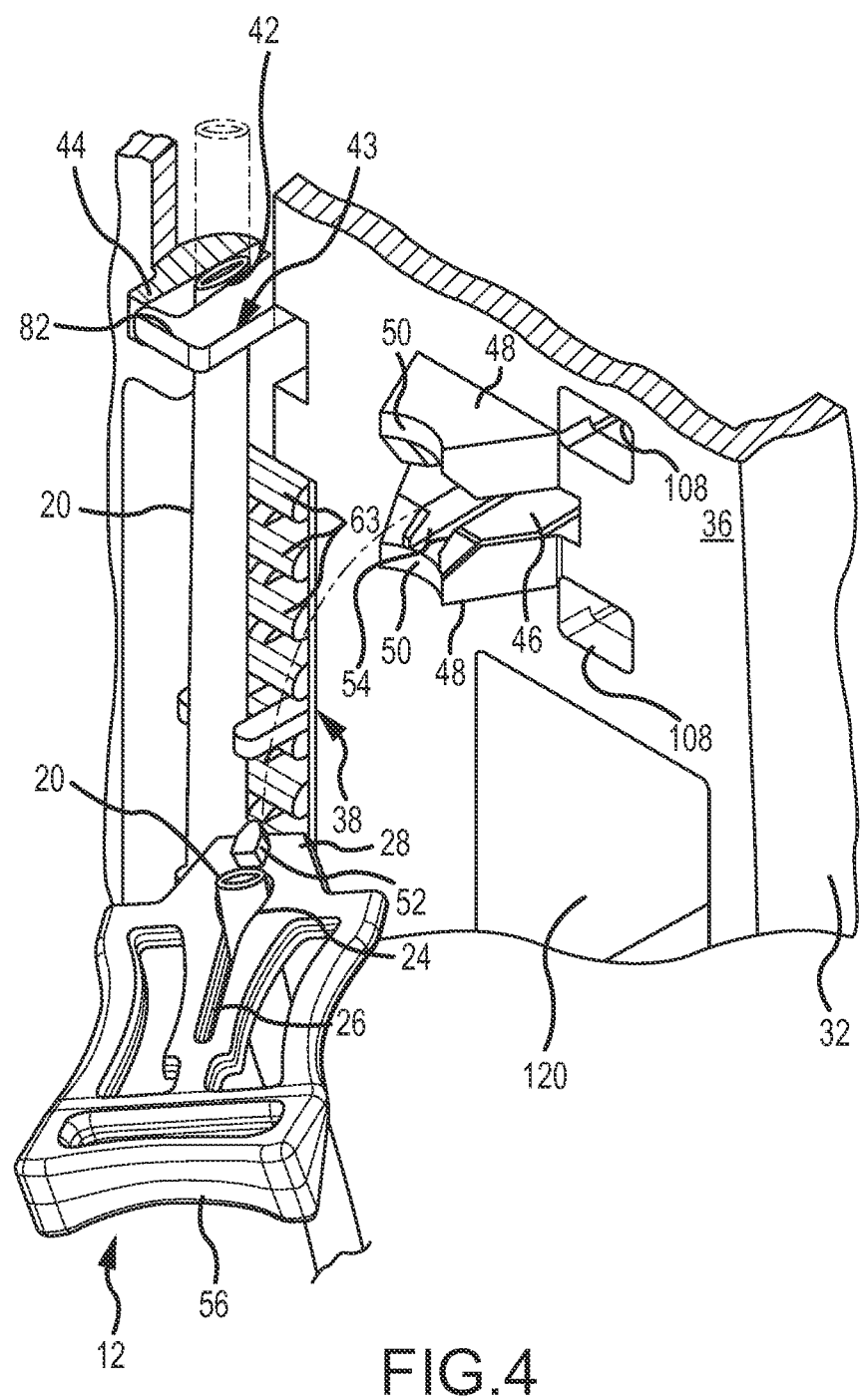
FIG. 4 is an enlarged partial perspective view of a portion of the infusion pump and the slide clamp moving into the position shown in FIG. 3.
Figure 5:
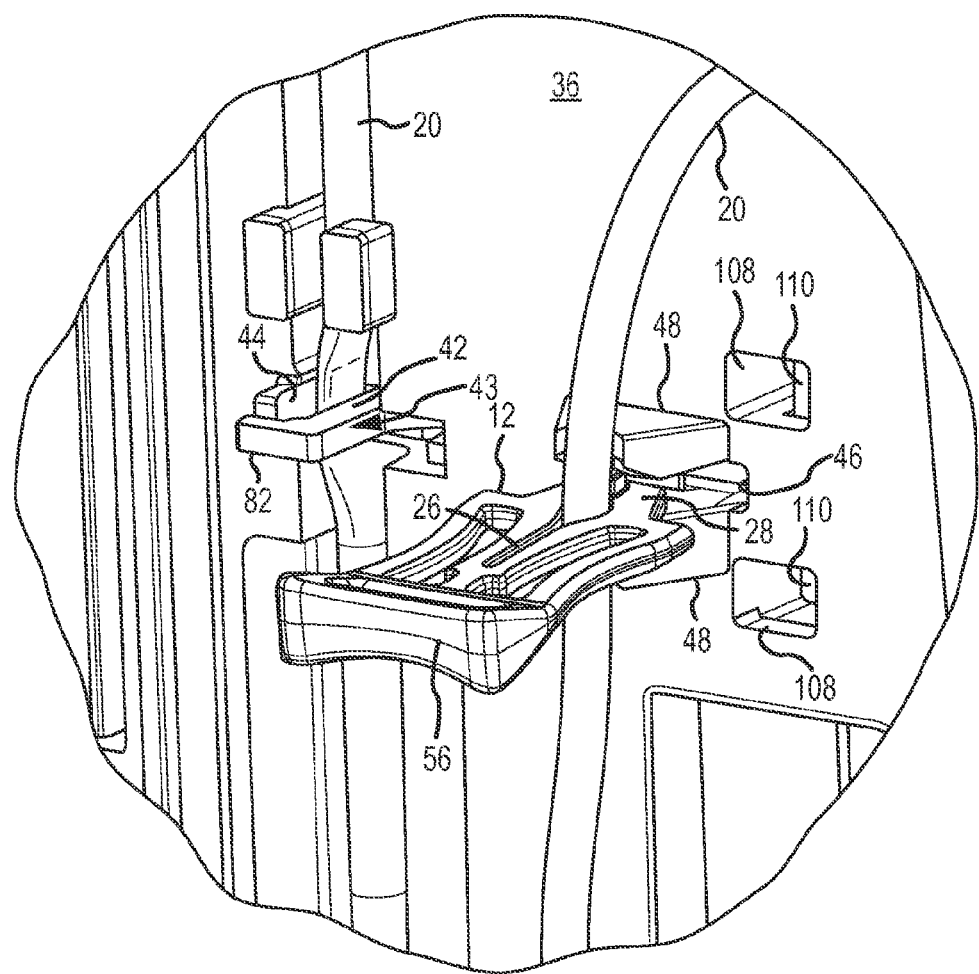
FIG. 5 is an enlarged partial perspective view of a portion of the infusion pump with the slide clamp and the delivery tube in the position shown in FIG. 3.
Figure 6:
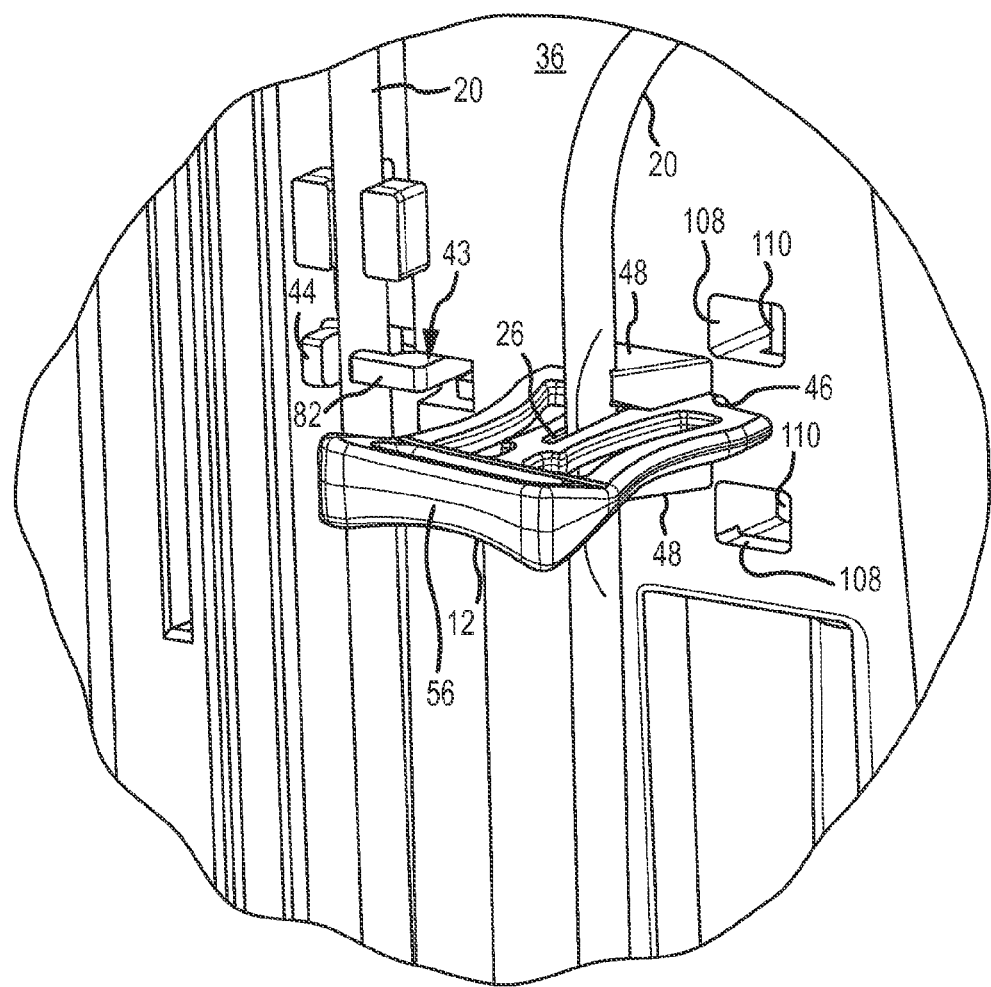
FIG. 6 is an enlarged partial perspective view similar to FIG. 5, showing the position of the slide clamp upon simultaneously releasing the internal occlusion clamp and occluding the delivery tube.
Figure 10:
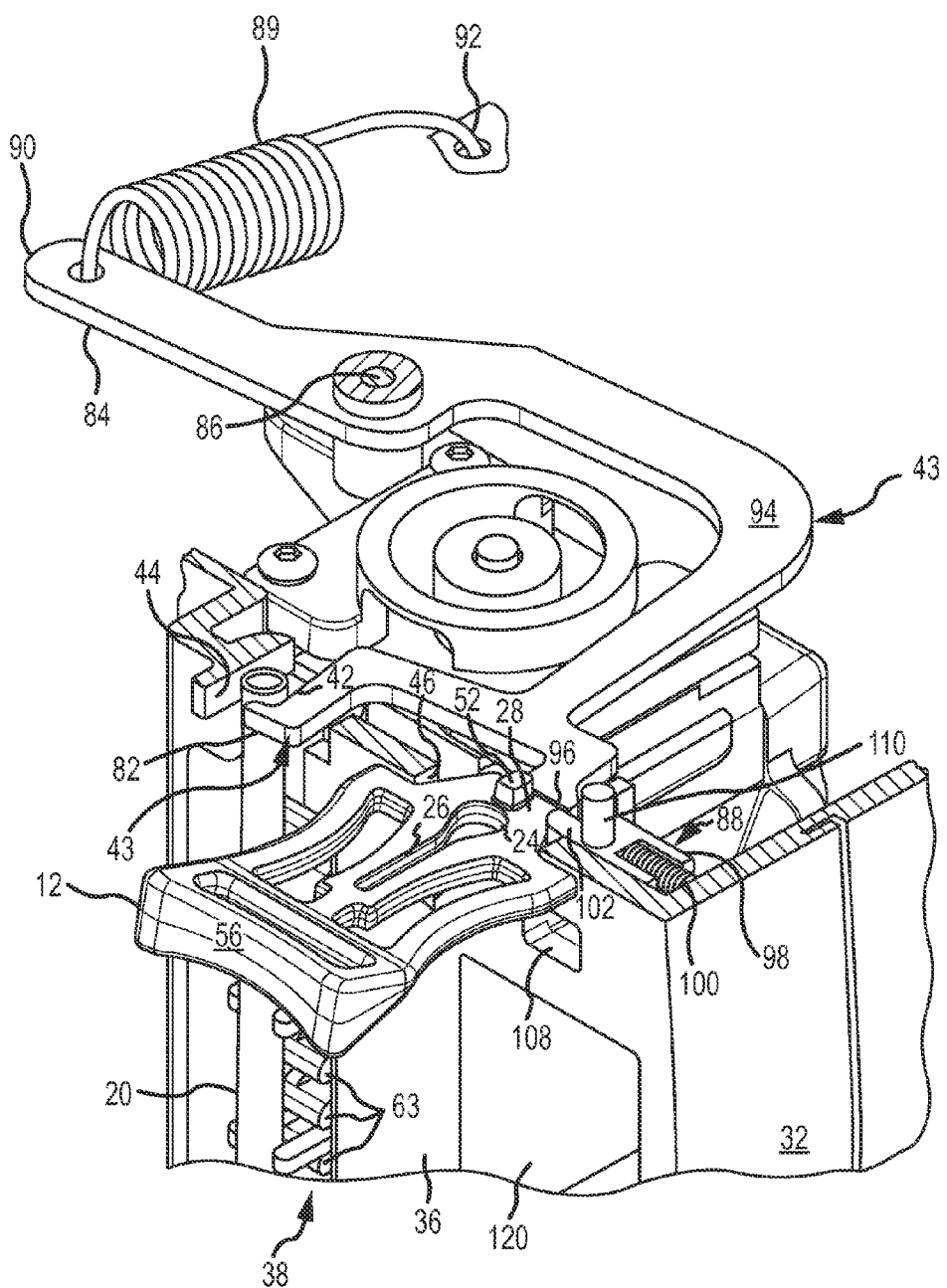
FIG. 10 is a enlarged partial perspective view similar to FIG. 9, in the position when the slide clamp releases the occlusion clamp.

The slide clamp 12 is retained around the delivery tube 20, preferably at a position midway between the bag 18 and the connector 22. As shown in FIGS. 4, 5 and 10, the delivery tube 20 extends through a rounded opening 24 in the slide clamp 12. The opening 24 has a diameter approximately equal to or very slightly smaller than an exterior diameter of the delivery tube 20. The position of the slide clamp 12 along the delivery tube 20 is adjustable by sliding the slide clamp 12 along the length of the delivery tube 20 while the delivery tube 20 is located in the opening 24. The close size relationship of the opening 24 and the diameter of the tube 20 frictionally maintains the slide clamp 12 at a desired position along a length of the delivery tube 20. When in the rounded opening 24, the delivery tube is not occluded to inhibit the flow of fluid. An occluding slot 26 extends rearwardly from the non-occluding opening 24. The slot 26 converges to create narrow transverse width into which the delivery tube 20 is forced when the delivery tube is occluded, as shown in FIG. 6. When the delivery tube 20 is forced into the slot 26, the sidewall of the delivery tube 20 is pinched together, thereby occluding the delivery tube 20 and preventing the flow of fluid 14. A trapezoid-shaped release tab 28 (FIGS. 4, 5 and 10) extends forward from a front or distal end of the slide clamp 12 at a position which is adjacent to and distal of the non-occluding opening 24.

Figure 2:
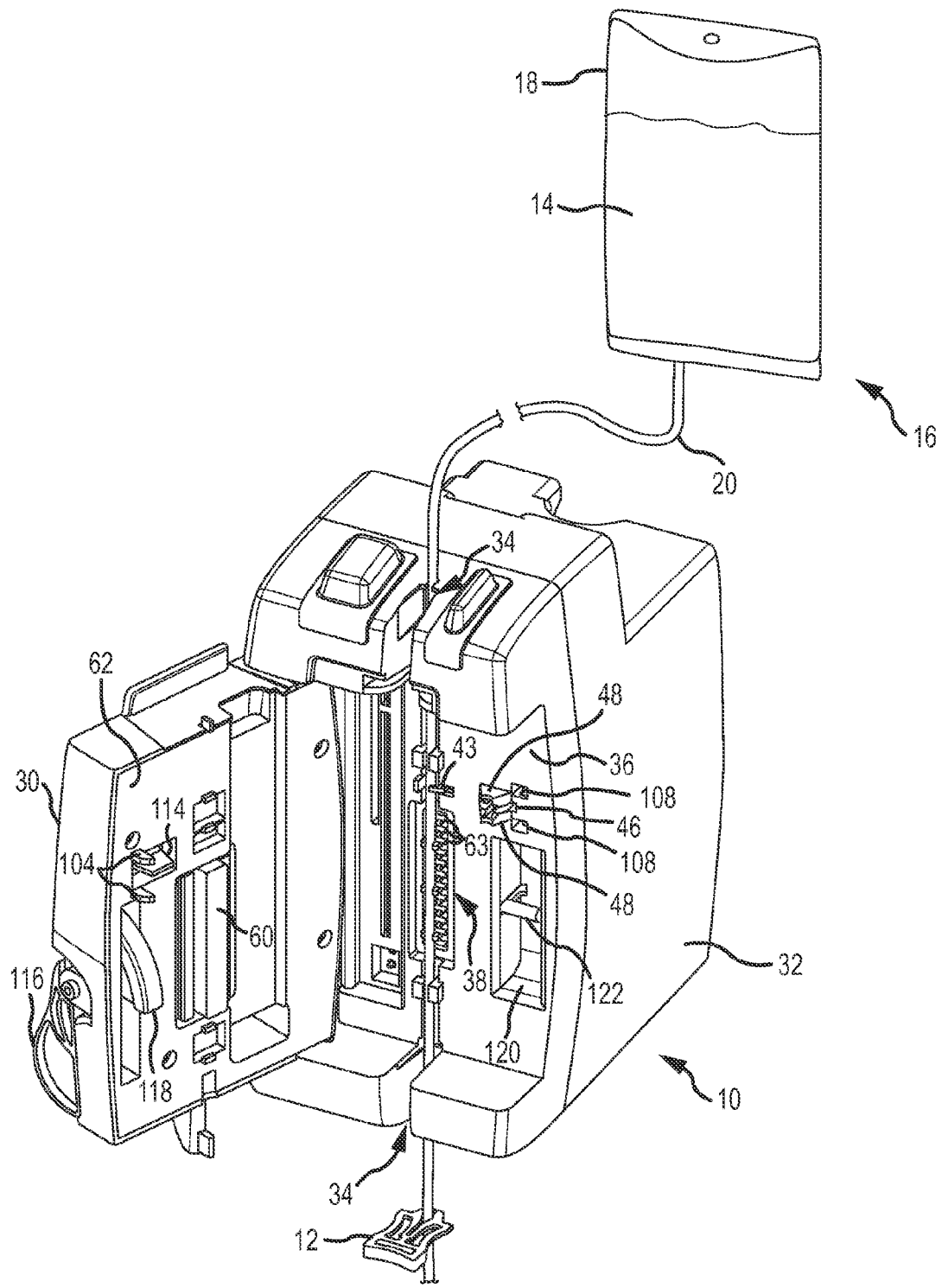
FIG. 2 is a perspective view similar to FIG. 1, shown with the front door of the infusion pump in an open position.
Figure 3:
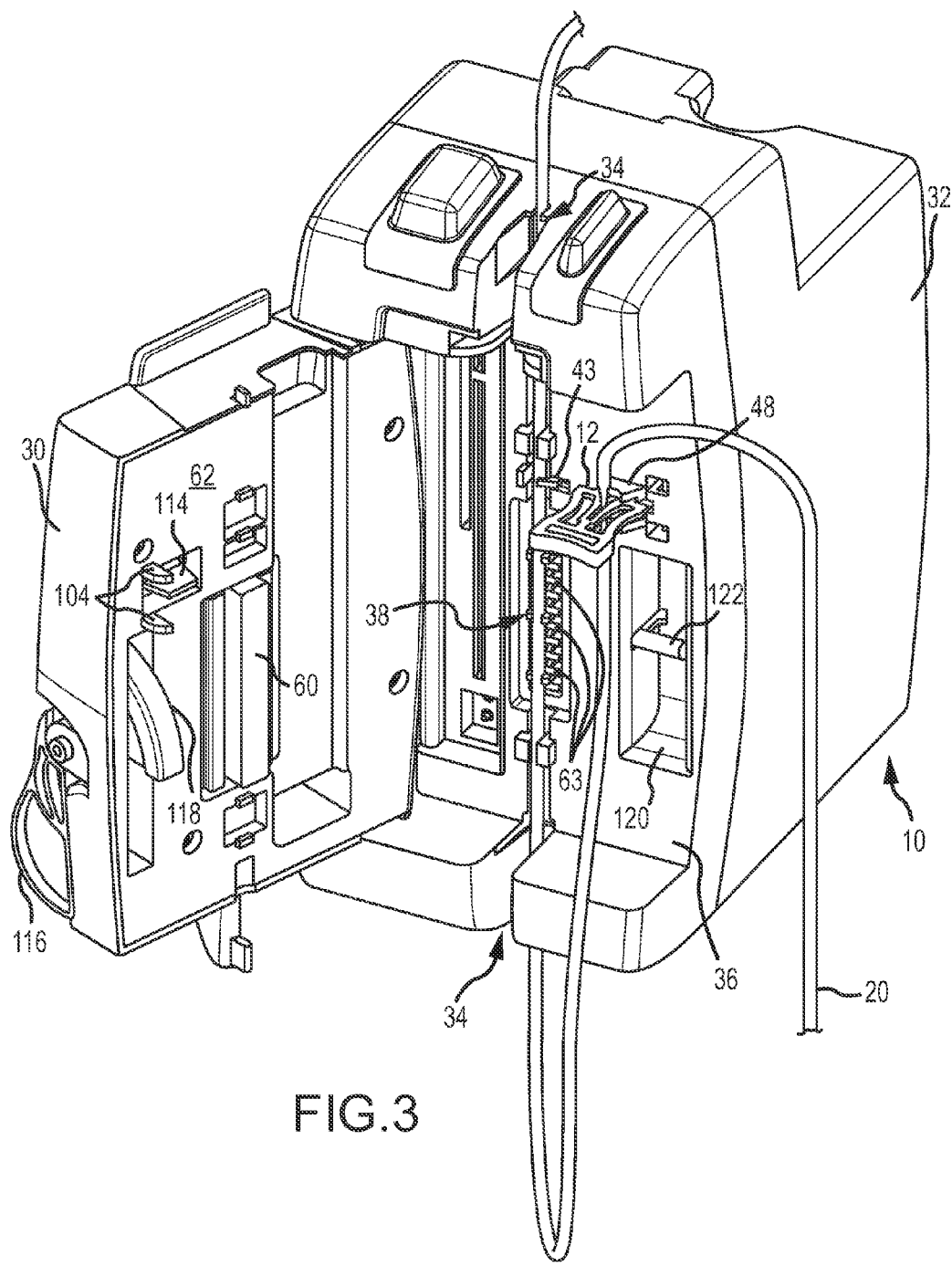
FIG. 3 is a perspective view similar to FIG. 2, showing the slide clamp moving into a position which will simultaneously release an internal occlusion clamp of the infusion pump and occlude the delivery tubing.

A front door 30 is pivotally attached to a main body 32 of the infusion pump 10, as shown in FIGS. 1, 2 and 3. A vertically-extending tubing channel 34 is located within a front panel 36 of the main pump body 32. The tubing channel 34 is accessible to receive a portion of the delivery tube 20 when the front door 30 is opened as shown in FIGS. 2 and 3. A conventional peristaltic pump 38 is located within the tubing channel 34 to compress and pinch the delivery tube 20 with the wavelike motion to move the fluid 14 through the delivery tube 20 when the door 30 is closed. The rate at which the peristaltic pump 38 operates controls the rate of flow of the fluid 14 through the delivery tube 20. The flow rate is programmed by attending medical personnel with the use of a conventional graphic interface 40 located on the exterior of the door 30.

The peristaltic pump 38 prevents the gravity-induced free flow of fluid 14 through the delivery tube 20 when the infusion pump is not operating, so long as the door 30 is closed. To prevent gravity-induced free flow of fluid 14 through the delivery tube 20 when the door 30 is opened, a compression edge 42 of an internal occlusion clamp 43 (FIGS. 9-11) compresses the delivery tube 20 against a stationary anvil 44 attached to the panel 36, thereby occluding the delivery tube when the door 30 is open. Closing the door 30 causes the internal occlusion clamp 43 to move the compression edge 42 away from the anvil 44 and open the delivery tube 20 to the fluid flow by operation of the peristaltic pump 38. When the door 30 is closed and the peristaltic pump 38 is not in operation, the peristaltic pump 38 blocks the flow of fluid 14 through the delivery tube 20.

A significant aspect of the present invention is using the slide clamp 12 as an actuator to release or open the internal occlusion clamp 43 while simultaneously moving the delivery tube 20 into the occluding slot 26, thereby pinching and occluding the delivery tube 20 with the slide clamp 12 when the occlusion clamp 43 is released or opened. In this manner, gravity-induced free flow of fluid 14 through the delivery tube 20 is prevented when the delivery tube 20 is released from the infusion pump. The anti-free flow requirements established by regulatory agencies and organizations are satisfied, by occluding the delivery tube with the slide clamp 12 at the same time that the slide clamp 12 is used as an actuator to release or open the internal occlusion clamp 43.

To remove the delivery tube 20 from the infusion pump 10 after having opened the door 20, the slide clamp 12 is manually positioned to insert the release tab 28 into an access opening 46 in the front panel 36 of the main body 32, as is understood by reference to FIGS. 3-6. Two tube supports 48 extend outward from the front panel 36 at locations above and below the access opening 46. Concave contact areas 50 (FIG. 4) are formed in the forward portions of the tube supports 48 at locations transversely centered about the access opening 46. As the release tab 28 of the slide clamp 12 is moved into the access opening 46 (FIG. 5), the delivery tube 20 is carried by the slide clamp 12 into a position where the delivery tube 20 above and below the slide clamp 12 contacts the contact areas 50. Further inward movement of the slide clamp 12 (FIG. 6) causes the release tab 28 to release or open the internal occlusion clamp 43 while the contact areas 50 hold the delivery tube 20 stationary and force the delivery tube 20 into the occluding slot 26 of the slide clamp 12. Thus, the inward movement of the slide clamp 12 simultaneously forces the delivery tube 20 into the occluding slot 26 of the slide clamp 12 while the slide clamp 12 releases the internal occlusion clamp 43. Once the internal occlusion clamp 43 has been released, the delivery tube 20 can be removed from the tubing channel 34 in the main body 32 of the infusion pump 10 because the compression edge 42 and the anvil 44 separate from one another. Gravity induced free flow of fluid through the removed delivery tube 20 is prevented by the occlusion from the slide clamp 12.

Projections 52 are formed on opposite sides of the front edge of the release tab 28, as shown in FIGS. 4, 5 and 10. The projections 52 fit into guide channels 54 formed in the tube supports 48 on opposite sides of the access opening 46. The projections 52 maintain the alignment of the release tab 28 within the access opening 46, to assure that the insertion of the slide clamp 12 positions the portion of the delivery tube 20 above and below the slide clamp in the contact areas 50. Such positioning assures that the further insertion of the slide clamp 12 into the access opening 46 moves the delivery tube into the occluding slot 26. The projections 52 also maintain the release tab 28 in position to release or open the internal occlusion clamp 43.

A proximal or rear wedge-shaped portion 56 of the slide clamp 12 is significantly thicker than the remaining forward portions of the slide clamp 12. The thickness of the slide clamp 12 through the region of the occluding slot 26 and the release tab 28 is generally uniform. The wedge-shaped portion 56 increases in thickness beginning at a position approximately proximal of the proximal end of the occluding slot 26. The wedge-shaped rear portion 56 is intended to be grasped between the first and second fingers of the user, while the thumb of the user contacts the rear surface of the wedge-shaped portion 56. The delivery tube 20 is located in front of the first and second fingers, and the thumb pushes the slide clamp 12 into the access opening 46. This configuration assists the user in manipulating the slide clamp 12 when inserting the release tab 28 into the access opening 46. The main body 32 of the infusion pump 10 may be held stationary by the user to counter the forces of pushing the slide clamp 12 to release the occlusion clamp 43 and to force the delivery tube 20 into the occluding slot 26 of the slide clamp 12.

Figure 8:
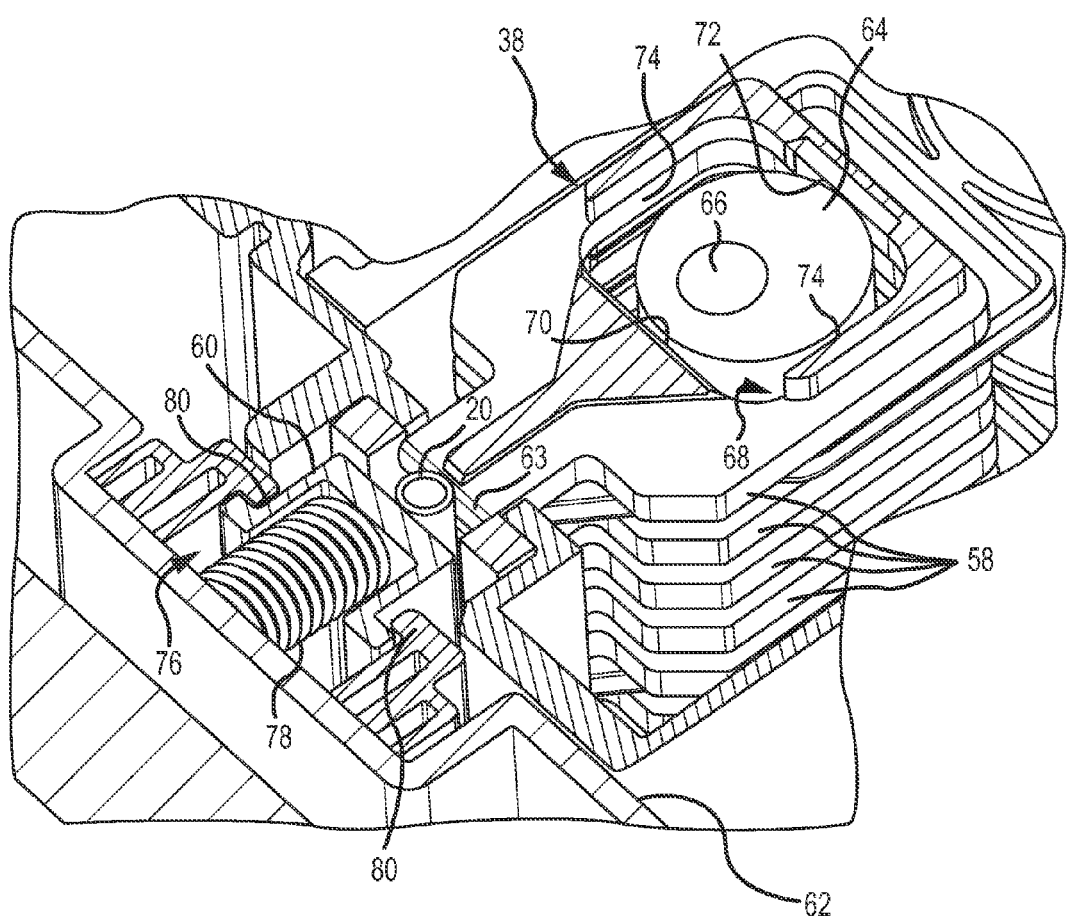
FIG. 8 is an enlarged partial perspective view of components of the peristaltic pump of the infusion pump which interact with the delivery tubing of the tubing set, when the delivery tube is retained in the infusion pump as shown in FIG. 1.

The peristaltic pump 38 is formed by a linear array of cam follower plungers 58 (FIG. 8) located in the tubing channel 34 and by a spring-loaded backplate 60 (FIGS. 8, 2 and 3) that is attached to an inner surface 62 of the door 30. The delivery tube 20 is loaded into the infusion pump 10 by positioning a portion of the delivery tube 20 within the tubing channel 34 as shown in FIG. 2. The spring-loaded backplate 60 presses the delivery tube 20 against contact edges 63 of the cam follower plungers 58 when the door 30 is closed, as shown in FIG. 8. The cam follower plungers 58 alternately and sequentially extend the contact edges 63 toward and away from the backplate 60 during operation of the peristaltic pump 38 to create an occlusion in the delivery tube 20 and move that occlusion sequentially through the peristaltic pump 38. One or more occlusions of the portion of the delivery tube within the peristaltic pump 38 exists due to this action. Operating in this manner, the peristaltic pump 38 continuously and controllably meters the fluid 14 through the delivery tube 20 toward the connector 22 and into the patient.

Each contact edge 63 of each of the cam follower plunger 58 moves forward and backward in the tubing channel 34 while pressing against the delivery tube 20 due to the action of a cam lobe 64 attached eccentrically to a shaft 66, as understood from FIG. 8. One cam lobe 64 is associated with each cam follower plunger 58. The cam lobe 64 is located within a rectangularly shaped opening 68 formed in the structure of each cam follower plunger 58. An electrical motor (not shown) rotates the shaft 66, causing the cam lobe 64 to rotate with the shaft 66. Due to its eccentric position on the shaft 66, the cam lobe 64 rotates into contact with a front surface 70 of the opening 68 to push the cam follower plunger 58 forward with the contact edge 63 against the delivery tube 20. Continued rotation of the shaft 66 causes the eccentric surface of the cam lobe 64 to push against a rear surface 72 of the opening 68, thereby moving the cam follower plunger 58 and the contact edge 63 rearwardly. The side surfaces 74 of the opening 68 may also contact the cam lobe 64 and cause the cam follower plungers 58 to pivot slightly from side to side. Attaching the separate cam lobes 64 at different rotationally displaced positions on the shaft 66 in sequence causes the wave-like sequential action of contact edges 63 of the cam follower plungers 58 against the delivery tube 20 from with rotation of the shaft 66.

Figure 7:
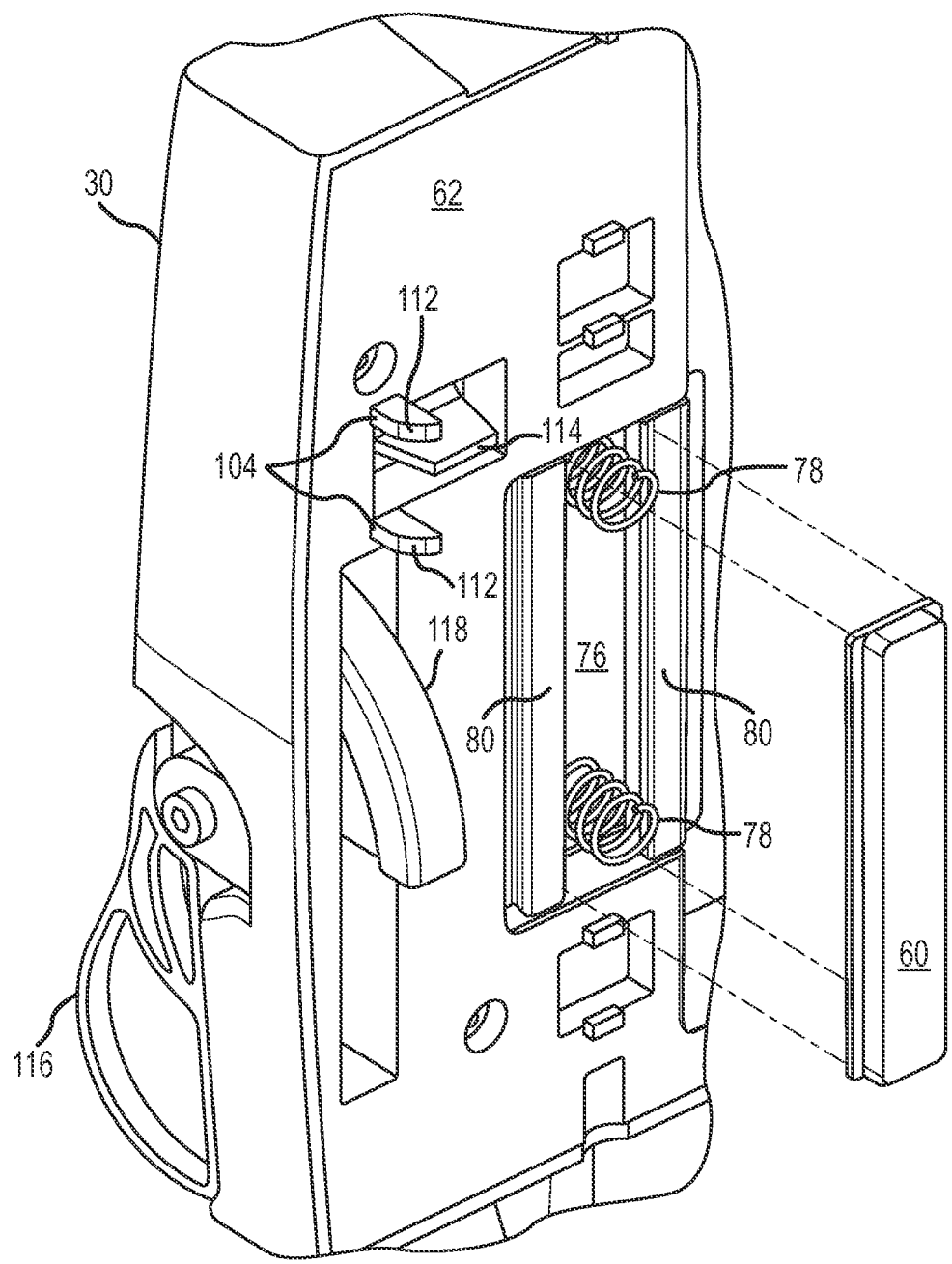
FIG. 7 is an enlarged partial perspective view of the front door of the infusion pump shown in FIG. 2, with components of a peristaltic pump of the infusion pump shown an exploded relationship.

The spring loaded backplate 60 is confined within a retaining area 76 formed in the inner surface 62 of the door 30, as shown in FIG. 7. Two or more springs 78 push the backplate 60 away from the door 30 and against a pair of retaining lips 80 which extend from the inner surface 62 and which form part of the retaining area 76. The backplate 60 withdraws into the door 30 from an extended position as shown in FIGS. 2, 3 and 8, when enough pressure is exerted on the exterior face or working surface of the backplate 60 by the portion of the delivery tube 20 compressed by the contact edges 63 of the cam follower plungers 58, to overcome the force exerted by the springs 78. The spring loaded backplate 60 supplies sufficient force against the delivery tube 20 to allow the contact edges 63 to occlude the delivery tube 20 when each cam follower plunger 58 is in its forwardmost position.

The door 30 of the infusion pump 10 must be closed for the peristaltic pump 38 to operate. A sensor (not shown) detects whether or not the door 30 is closed and allows the operation of the peristaltic pump 38 only when the door 30 is closed. At least one contact edge 63 of one cam follower plunger 58 is always occluding the delivery tube 20 when the door 30 is closed, whether or not the peristaltic pump 38 is operating. Since the delivery tube 20 is always occluded when the door 30 is closed, the fluid 14 is prevented from flowing freely by gravity through the delivery tube 20 when the door 30 is closed.

Figure 9:
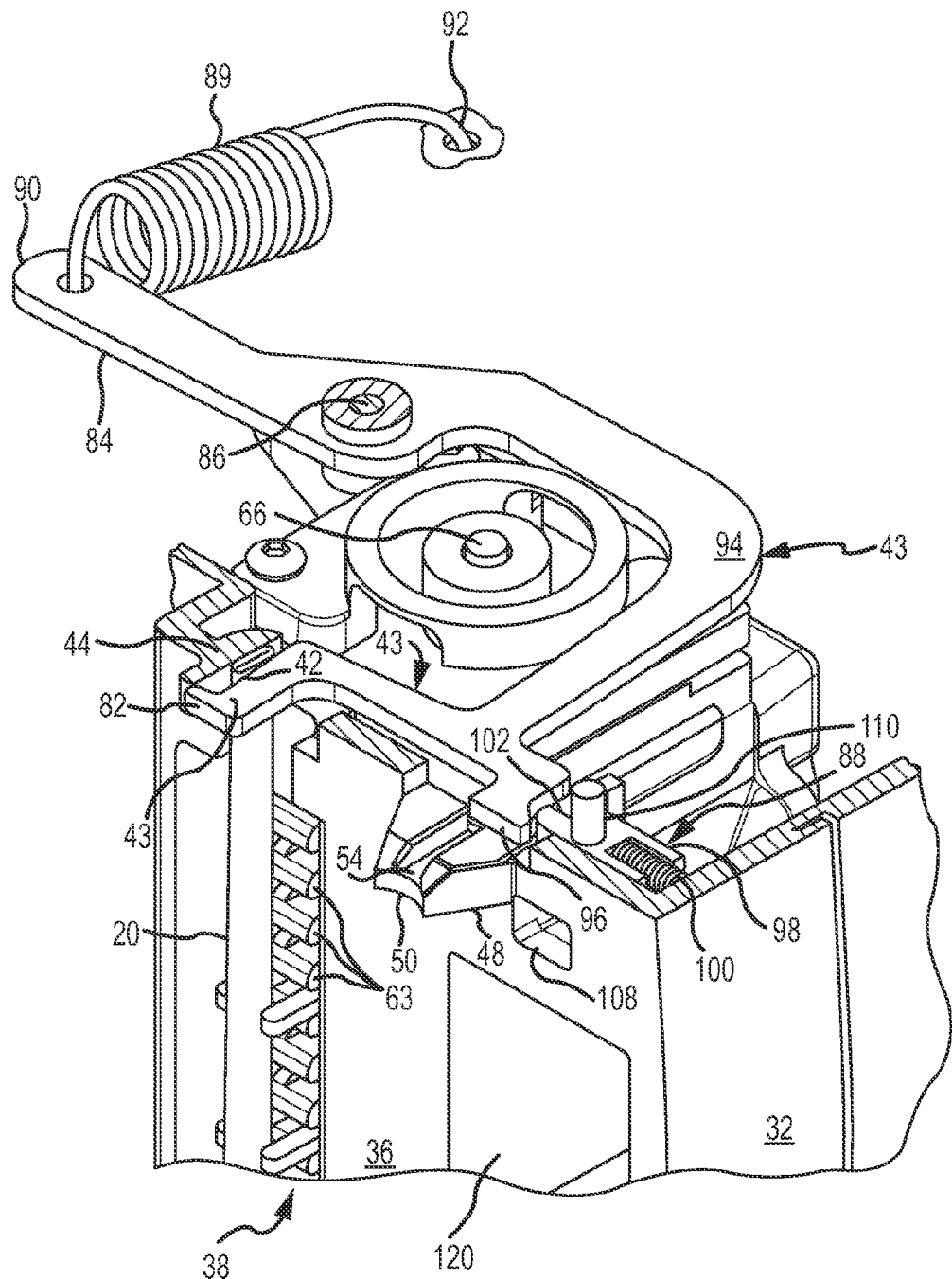
FIG. 9 is an enlarged partial perspective view of components of the internal occlusion clamp of the infusion pump, in the position when the door is opened as shown in FIG. 2.
Figure 11:
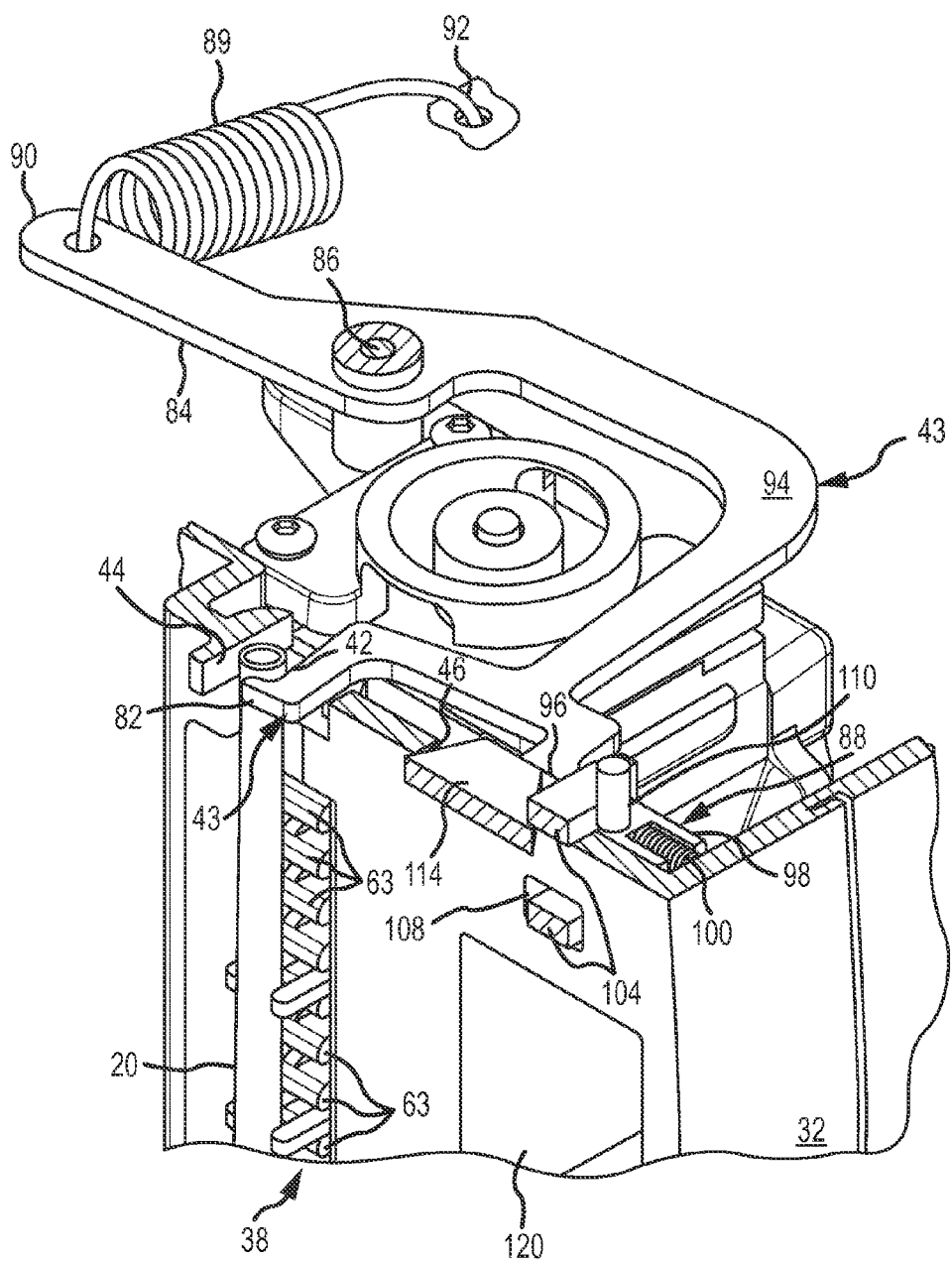
FIG. 11 is an enlarged partial perspective view similar to FIG. 10, in the position where the internal occlusion clamp is opened by closure of the front door as shown in FIG. 1.

To prevent the free flow of the fluid 14 through the delivery tube 20 when the door 30 is opened, the occlusion clamp 43 moves into a clamping or occluding position shown in FIG. 9 from an open or released position shown in FIGS. 10 and 11. The compression edge 42 of the occlusion clamp 43 presses the delivery tube 20 against the anvil 44 to occlude the delivery tube when the occlusion clamp 43 is in the clamping position. A blocking lip 82 extends from the compression edge 42 around the delivery tube 20 and across the gap between the compression edge 42 and the anvil 44 and slightly overlaps the anvil 44, as shown in FIGS. 4 and 9, to prevent the forcible removal of the delivery tube 20 from between the compression edge 42 and the anvil 44 when the occlusion clamp 43 is in the clamping position.

The occlusion clamp 43 includes a lever 84 which pivots about a pivot point 86 to establish the clamping position (FIG. 9) and the open position (FIGS. 10 and 11). A lever lock mechanism 88 (FIG. 12) holds the lever 84 in the open position when the slide clamp 12 releases the occlusion clamp 43 when the door 30 of the infusion pump 10 is open. The lever 84 is biased into the clamping position by a bias spring 89 connected between an arm 90 of the lever 84 and a connection point 92 within the main body 32 of the infusion pump 10. Another arm 94 of the lever 84 extends on the opposite side of the pivot point 86 and locates the compression edge 42 at a position for interaction with the anvil 44. The other arm 94 also locates a release surface 96 (FIG. 9) formed on the lever arm 94 at a location which is directly behind the access opening 46 (FIG. 4) in the front panel 36 of the main body 32. The bias spring 89 forces the compression edge 42 toward the anvil 44 and forces the release surface 96 toward the access opening 46.

The lever 84 is similar to a lever used in an internal occlusion clamp of a prior art infusion pump, except for the blocking lip 82 and the release surface 96. In the conventional infusion pump, the blocking lip 82 is not used. Without the blocking lip 82, the delivery tube can be forcibly removed from between the compression edge 42 and the anvil 44. In the prior art infusion pump, the release surface 96 does not exist but instead a portion of the lever 84 continues forward and extends outside of the front panel 36. The portion of the lever which extends forward from the front panel terminates in a contact, which is manually depressed by finger pressure of the user to open or release the internal occlusion clamp after the door has been opened.

The lever lock mechanism 88 includes a plunger 98 which moves between a retracted position shown in FIG. 11 and an extended position shown in FIGS. 9 and 10. A spring 100 extends from within a recess in the plunger 98 to contact a surface of the main body. The spring 100 biases the plunger 98 toward the lever arm 94. A retaining edge 102 of the plunger 98 extends in front of and past the release surface 96 on the lever arm 94. The retaining edge 102 of the plunger 98 holds the lever 84 to establish the open position of the occlusion clamp 43. The release tab 28 of the slide clamp 12 contacts the release surface 96 of the lever arm 94 through the access opening 46, and further insertion force applied to the slide clamp 12 pivots the lever 84 sufficiently so that the retaining edge 102 of the plunger 98 extends in front of the release surface 96. With the plunger 98 in the extended position with the retaining edge 102 overlapping the release surface 96, the lever 84 is pivoted so that the occlusion clamp 43 is in the open position. The bias spring 89 supplies enough pivoting force on the arm 84 to maintain sufficient frictional contact between the release surface 96 and the retaining edge 102 to hold the occlusion clamp 43 in the open position.

Once the plunger 98 is in the extended position with the retaining edge 102 overlapping the release surface 96, the occlusion clamp 43 can only be released by closing the door 30. Releasing the occlusion clamp 43 is accomplished by moving the plunger 98 to a retracted position where the retaining edge 102 is withdrawn from contact with the release surface 96, thereby allowing the lever arm 94 to pivot slightly forward.

Figure 12:
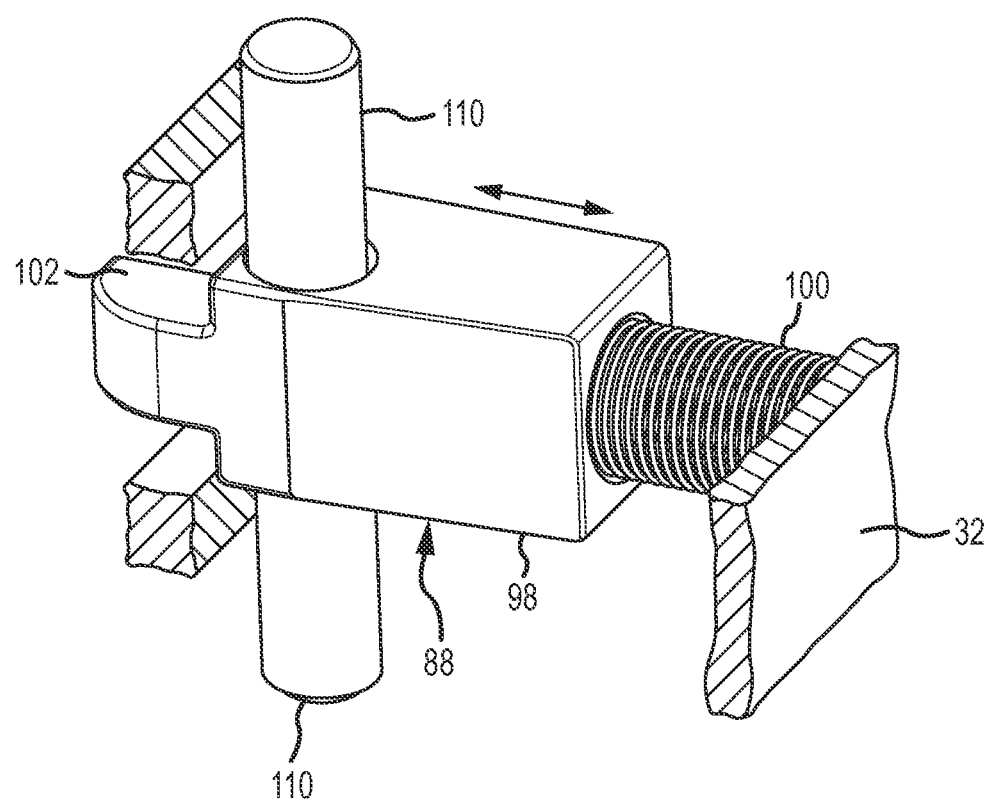
FIG. 12 is an enlarged partial perspective view of a slidable lock of the internal occlusion clamp, also shown in FIGS. 9-11.

Moving the plunger 98 to the retracted position is accomplished by two release projections 104 which protrude from the inner surface 62 of the door 30 (FIGS. 2 and 3). As the door 30 is closed from the open position (FIG. 2), the door release projections 104 extend through openings 108 in the front panel 36 of the main body 32 and contact upper and lower portions of a slide pin 110 which extends vertically upward and downward from the plunger 98 (FIGS. 11 and 12). Ramp surfaces of the door release projections 104 contact the slide pin 110, and move the plunger to the retracted position by camming action as the door 30 closes.

A door release tab 114 extends from the inner surface 62 of the door 30 into the access opening 46 when the door is closed. The door release tab 114 contacts the release surface 96 of the lever arm 94, and holds the lever 84 in the position to release and open the occlusion clamp 43 when the door 30 is closed, as shown in FIGS. 10 and 11.

The retaining edge 102 of the plunger 98 is moved laterally to the side of the release surface 96, so that upon opening the door 30, the plunger 98 does not prevent the lever 84 from pivoting to the occluding position. The plunger 98 of the lever lock mechanism 88 does not prevent the lever 84 from pivoting into the position to occlude the delivery tube 20 after the door 30 has been closed and when the door is opened. The plunger 98 of the lever lock mechanism 88 holds the lever 84 in the open position only after the slide clamp 12 has been used as an actuator to release the occlusion clamp 43 to its open position.

A door latch lever 116 is pivotally connected to the door 30, as shown in FIGS. 1-3. The door latch lever 116 locks the door 30 to the body 32 when the lever 116 is pivoted into the closed position (FIG. 1). Pivoting the door latch lever 116 in the opposite direction unlocks the door 30 and allows it to open to the open position (FIG. 2). An arc shaped portion 118 of the door latch lever 116 extends into a recess area 120 formed on a front panel 36 of the main body 32. The arc shaped portion 118 engages a latch pin 122 which extends across a portion of the recess area 120. Pivoting movement of the door latch lever 116 causes the arc shaped portion 118 to move relative to the latch pin 122 and pull the door 30 firmly against the front panel 36 of the main body 32. Pivoting the door latch lever 116 in the opposite direction opens the door by releasing the arc shaped portion 118 from the latch pin 122.

To release the occlusion clamp 43 from occluding the delivery tube 20 (FIGS. 6, 10 and 11), the slide clamp 12 is orientated horizontally and positioned such that the release tab 28 of the slide clamp 12 is adjacent to the access opening 46, as understood from FIGS. 4 and 5. The projections 52 of the slide clamp 12 extend into the guide channels 54 (FIG. 5). The release tab 28 is forced into contact with the release surface 96 of the lever arm 94 while portions of the delivery tube 20 immediately above and below the slide clamp 12 move into contact with the concave contact areas 50 (FIG. 5) of the tube supports 48, as shown in FIGS. 6, 10 and 11. The thick rear wedge-shaped portion 56 of the slide clamp 12 is pushed by force from the users thumb while the slide clamp 12 is maintained in alignment between the tube supports 48 by the projections 52 in the guide channels 54. As the release tab 28 of the slide clamp 12 moves forward while in contact with the release surface 96 of the lever arm 94, the lever 84 pivots into the position where the retaining edge 102 of the plunger 98 extends in front of and overlaps with the release surface 96 to thereby hold the lever 84 and establish the open position of the occlusion clamp 43 simultaneously while the portion of the delivery tube 20 within the slide clamp 12 is forced from the non-occluding opening 24 into the occluding slot 26. The simultaneous occurrence of these two events effectively maintains, and transfers, the location of the occlusion from the occlusion clamp 43 to the slide clamp 12.

After the delivery tube 20 has been occluded by the slide clamp 12 in the manner described, any further use of the delivery tube will require the user to manually move the slide clamp 12 relative to the delivery tube 20 so that the delivery tube extends through the non-occluding opening 24. Even if the delivery tube is inserted into the infusion pump and the infusion pump is operated, there will be no fluid flow through the delivery tube until the delivery tube 20 is moved into the non-occluding opening 24 of the slide clamp 12. This requirement establishes the necessity for an additional safety-related manual action before fluid will flow through the delivery tube.

Since use of the slide clamp 12 is required to release the delivery tube 20 from the occlusion clamp 43, there is a reduced or eliminated possibility that a free flow condition through the delivery tube 20 will occur when the delivery tube 20 is removed from the infusion pump 10. The infusion pump 10 as shown and described in relation to this invention is simpler in operation and construction than previously known anti-free flow infusion pumps. The infusion pump 10 and slide clamp 12 combination is also less costly to manufacture, and allows their use together in the manner which makes it relatively easy and straightforward to train medical personnel in the proper and safe use of the equipment.

A presently preferred embodiment of the present invention and many of its improvements have been described with a degree of particularity. This description is of a preferred example of implementing the invention, and is not necessarily intended to limit the scope of the invention. The scope of the invention is defined by the following claims.

What is claimed:

1. An infusion pump which flows medicinal fluid through a delivery tube of an infusion tubing set to a patient and which prevents the free flow of fluid through the delivery tube, the tubing set including a slide clamp having a opening through which the delivery tube extends, the opening including a non-occluding portion and an adjoining occluding portion, the non-occluding portion allowing fluid flow through the delivery tube when the delivery tube is located in the non-occluding portion, the occluding portion preventing fluid flow through the delivery tube when the delivery tube is located in the occluding portion, the slide clamp further including a release tab extending adjacent the non-occluding portion, the infusion pump comprising:

a tubing channel which receives a first portion of the delivery tube;

a pumping device operative in the tubing channel and with the delivery tubing to flow the fluid through the delivery tube;

an anvil attached on one side of the tubing channel;

a pivotal lever having a compression edge which moves from the side of the tubing channel opposite the anvil into adjacency with the anvil to compress the delivery tube against the anvil and prevent fluid flow through the delivery tube when the pivotal lever is pivoted into an occluding position, the compression edge also moves away from adjacency with the anvil to open fluid flow through the delivery tube when the pivotal lever is pivoted into a non-occluding position, the pivotal lever also having a release surface which when moved a sufficient distance pivots the pivotal lever to move from the occluding position to the non-occluding position;

an access opening adapted to receive the release tab of the slide clamp upon insertion and to direct the release tab into contact with the release surface of the pivotal lever, the access opening accommodating insertion of the release tab to the sufficient distance to pivoted the pivotal lever from the occluding position to the non-occluding position;

at least one tube support positioned adjacent to the access opening to contact and maintain the delivery tube in a stationary position during the insertion of the release tab to the sufficient distance;

a lever lock mechanism to releasably hold the pivotal lever in the non-occluding position after the insertion of the release tab has moved the release surface of the pivotal lever the sufficient distance; and the tube support causes the delivery tube to move from the non-occluding portion of the slide clamp into the occluding portion of the slide clamp simultaneously with insertion of the release tab to the sufficient distance to pivot the pivotal lever to the non-occluding position.

2. An infusion pump as defined in claim 1, further comprising:

a main body to which the anvil, the pivotal lever and the access opening are connected;

a door pivotally attached to the main body, the door pivoting between a closed position which prevents access to the first portion of the delivery tube in the tubing channel and an open position which allows access to the first portion of the delivery tube in the tubing channel; and a door release tab which protrudes from the door into the access opening to contact the release surface and pivot the pivotal lever to the non-occluding position when the door is closed.

3. An infusion pump as defined in claim 2, wherein:

the lever lock mechanism comprises a plunger having a retaining edge which is transversely movable to overlap the release surface of the pivotal to hold the internal occlusion clamp in the non-occluding position, and a slide pin extending transversely from the plunger;

the infusion pump further comprises an release opening extending from the slide pin; and the door further includes a door release projection which protrudes from the door into the release opening to contact the slide pin and move the plunger to separate the retaining edge from the overlapping relationship with the release surface of the pivotal lever to allow the pivotal lever to assume the non-occluding position when the door is closed.

4. An infusion pump as defined in claim 3, wherein:

the plunger further allowing the pivotal lever to assume the occluding position when the door is opened after having been closed.

5. An infusion pump as defined in claim 2, wherein:

the main body includes a front panel which faces toward the door;

the pivotal lever is located behind the front panel;

the access opening extends from the front panel rearwardly to the release surface of the pivotal lever; and each tube support projects outward from the front panel toward the door.

6. An infusion pump as defined in claim 5, wherein:

the door covers the access opening and each tube support when the door is the closed position.

7. An infusion pump as defined in claim 6, wherein:

the slide clamp and the second portion of the delivery tube are located outside of the main body and the door when the door is in the closed position.

8. An infusion pump as defined in claim 5, wherein:

one tube support is positioned on opposite sides of the access opening and immediately adjacent to the access opening to contact and maintain the delivery tube in a stationary position on both opposite sides of the slide clamp.

9. An infusion pump as defined in claim 8, wherein:

each tube support includes a guide channel which faces toward the access opening and toward the guide channel of the opposite tube support; and the slide clamp includes a pair of projections which extend on opposite sides adjacent to the release tab and which move in the guide channels of the tube supports during insertion movement of the release tab into the access opening to move the release surface of the pivotal lever the sufficient distance.

10. An infusion pump as defined in claim 1, wherein:

the pivotal lever further includes a blocking lip extending from the compression edge to and overlapping with the anvil to block removal of the delivery tube from between the compression edge and the anvil when the pivotal lever is in the occluding position.

11. An infusion pump as defined in claim 1 wherein:

the tube support includes a guide channel which extends toward the access opening; and the slide clamp includes a projection adjacent to the release tab which moves within the guide channel during insertion movement of the release tab into the access opening to move the release surface of the pivotal lever of the sufficient distance.

12. An infusion pump as defined in claim 1, wherein:

singular manual insertion of the release tab into the access opening to the sufficient distance to pivot the pivotal lever from the occluding position to the non-occluding position simultaneously moves the delivery tube from the non-occluding portion of the opening in the slide clamp into the occluding portion of the opening in the slide clamp.

13. An infusion pump as defined in claim 1, wherein:

one tube support is positioned on opposite sides of the access opening and immediately adjacent to the access opening to contact and maintain the delivery tube in a stationary position on both opposite sides of the slide clamp.

14. An infusion pump as defined in claim 1, wherein:

the access opening requires manual manipulation of the slide clamp for insertion of the release tab to the sufficient distance to pivot the pivotal lever from the occluding position to the non-occluding position.

15. An infusion pump which flows medicinal fluid through a delivery tube of an infusion tubing set to a patient and which prevents the free flow of fluid through the delivery tube, the tubing set including a slide clamp having a opening through which the delivery tube extends, the opening including a non-occluding portion and an adjoining occluding portion, the non-occluding portion allowing fluid flow through the delivery tube when the delivery tube is located in the non-occluding portion, the occluding portion preventing fluid flow through the delivery tube when the delivery tube is located in the occluding portion, the infusion pump comprising:

a tubing channel which receives a first portion of the delivery tube;

a pumping device operative in the tubing channel and with the first portion of the delivery tubing to flow the fluid through the delivery tube;

an internal occlusion clamp which interacts with the delivery tube and which has an occluding position for occluding the delivery tube when the first portion of the delivery tube in the tubing channel is accessible to a user of the infusion pump and a non-occluding position for allowing fluid flow through the delivery tube when the first portion of the delivery tube in the tubing channel is not accessable to the user of the infusion pump;

an access opening adapted to receive a portion of the slide clamp when manually inserted therein by the user of the infusion pump;

a release actuator of the internal occlusion clamp which when actuated releases the internal occlusion clamp from the occluding position and moves the internal occlusion clamp to the non-occluding position, the release actuator located relative to the access opening for contact by the portion of the slide clamp inserted through the access opening, the release actuator becoming actuated by movement to a sufficient distance imparted from the portion of the slide clamp inserted through the access opening;

at least one tube support positioned adjacent to the access opening to contact and maintain the delivery tube in a stationary position at the access opening during the insertion of the portion of the slide clamp to the sufficient distance; and the stationary position of the delivery tube maintained by tube support causes manual insertion of the portion of the slide clamp in the access opening to the sufficient distance to move the delivery tube from the non-occluding portion of the opening in the slide clamp into the occluding portion of the opening in the slide clamp simultaneously with actuating the release mechanism.

16. An infusion pump as defined in claim 15, further comprising:

a main body to which the internal occlusion clamp and the access opening are connected;

a door pivotally attached to the main body, the door pivoting between a closed position which prevents access to the first portion of the delivery tube in the tubing channel and an open position which allows access to the first portion of the delivery tube in the tubing channel; and wherein:

the slide clamp and the second portion of the delivery tube are located outside of the main body and the door when the door is in the closed position.

17. An infusion pump as defined in claim 16, wherein:
the door covers the access opening, each tube support and the tubing channel when the door is the closed position.

18. An infusion pump as defined in claim 17, further comprising:

a tab which protrudes from the door into the access opening to actuate the release actuator when the door is closed.

19. An infusion pump as defined in claim 16, further comprising:

a holding mechanism which releasably holds the internal occlusion clamp in the non-occluding position after the release actuator has been actuated;

an release opening extending from the front panel to the holding mechanism; and a release projection which protrudes from the door into the release opening to contact the holding mechanism and release the holding relationship and allow the internal occlusion clamp to assume the non-occluding position when the door is closed.

20. An infusion pump as defined in claim 19, wherein:
the holding mechanism comprises a plunger which is transversely movable to overlap a portion of the internal occlusion clamp when in the non-occluding position;

the infusion pump further comprises an release opening formed in the main body and covered by the door when the doors in the closed position;

the door further includes a door release projection which protrudes from the door into the release opening to move the plunger to separate the plunger from the overlapping relationship with the portion of the internal occlusion clamp to allow the internal occlusion clamp to assume the non-occluding position when the door is closed.

21. An infusion pump as defined in claim 15, wherein:
one tube support is positioned on opposite sides of the access opening and immediately adjacent to the access opening to contact and maintain the delivery tube in a stationary position on both opposite sides of the slide clamp.

22. An infusion pump as defined in claim 21, wherein:
each tube support includes a guide channel which faces toward the access opening and toward the guide channel of the opposite tube support; and the slide clamp includes a pair of projections which extend on opposite sides of the slide clamp and which move in the guide channels of the tube supports during insertion movement of the portion of the slide clamp into the access opening to the sufficient distance to actuate the release actuator.

23. An infusion pump as defined in claim 15, wherein the internal occlusion clamp comprises:

an anvil attached on one side of the tubing channel;

a pivotal lever having a compression edge which moves from the side of the tubing channel opposite the anvil into adjacency with the anvil when the internal occlusion clamp is in the occluding position and which moves away from adjacency with the anvil when the internal occlusion clamp is in the non-occluding position, the first portion of the delivery tube located between the anvil and the compression edge when the first portion of the delivery tube is located in the tubing channel; and the release actuator including a release surface of the pivotal lever located behind the access opening.

24. An infusion pump as defined in claim 23, wherein:
the pivotal lever further includes a blocking lip extending from the compression edge to overlap with the anvil to block removal of the delivery tube from between the compression edge and the anvil when the internal occlusion clamp is in the occluding position.

* * * * *

UNITED STATES PATENT AND TRADEMARK OFFICE
CERTIFICATE OF CORRECTION

PATENT NO. : 8,465,464 B2  
APPLICATION NO. : 12/852116  
DATED : June 18, 2013  
INVENTOR(S) : Lee W. Travis et al.

Page 1 of 1

It is certified that error appears in the above-identified patent and that said Letters Patent is hereby corrected as shown below:

In the Specification:
Column 4, line 27, delete "accessable," and substitute therefor --accessible--.
Column 6, line 8, delete "accessable," and substitute therefor --accessible--.

In the Claims:
Claim 1, column 13, line 1, delete "pivoted," and substitute therefor --pivot--.
Claim 3, column 13, line 34, after the word "pivotal" insert --lever--.
Claim 3, column 13, line 37, delete "an" and substitute therefor --a--.
Claim 7, column 13, line 62, delete the second occurrence of "the" and substitute therefor --a--.
Claim 11, column 14, line 26, delete the second occurrence of "of.".
Claim 15, column 14, line 50, delete "a" and substitute therefor --an--.
Claim 15, column 14, line 62, delete "tubing" and substitute therefor --tube--.
Claim 15, column 15, line 4, delete "accessable" and substitute therefor --accessible--.
Claim 15, column 15, line 29, delete "mechanism" and substitute therefor --actuator--.
Claim 16, column 15, line 40, delete the second occurrence of "the" and substitute therefor --a--.
Claim 19, column 15, line 55, delete "an" and substitute therefor --a--.
Claim 19, column 15, line 55, delete "the front panel" and substitute therefor --in the main body--.
Claim 19, column 16, line 3, delete "relationship" and substitute therefor --mechanism--.
Claim 20, column 16, line 10, delete "the infusion pump further comprises an" and substitute therefor --the--.
Claim 20, column 16, line 10, after "opening" insert --is--.
Claim 20, column 16, line 13, delete "doors" and substitute therefor --door is--.

Signed and Sealed this  
Twenty-fourth Day of June, 2014

Michelle K. Lee  
*Deputy Director of the United States Patent and Trademark Office*